United States Patent [19]

Lane et al.

[11] Patent Number: 5,012,030
[45] Date of Patent: Apr. 30, 1991

[54] PROCESS FOR PREPARING POLYBUTENES WITH INCREASED REACTIVITY

[75] Inventors: Kelley R. Lane, Winfield; Wayne P. Schammel, Naperville, both of Ill.

[73] Assignee: Amoco Corporation, Chicago, Ill.

[21] Appl. No.: 418,855

[22] Filed: Oct. 10, 1989

[51] Int. Cl.$^5$ ................................................. C07C 2/02
[52] U.S. Cl. ..................................... 585/527; 585/532
[58] Field of Search ........................... 585/527, 532

[56] References Cited

U.S. PATENT DOCUMENTS

| | | | |
|---|---|---|---|
| 2,076,201 | 4/1937 | Langedijk | 585/532 |
| 3,073,876 | 1/1963 | McMaster | 585/532 |
| 3,119,884 | 1/1964 | Allen et al. | 585/517 |
| 3,655,808 | 4/1972 | Driscoll | 585/527 |
| 3,842,134 | 10/1974 | Pratt | 585/532 |
| 4,465,887 | 8/1984 | Schammel | 585/517 |
| 4,558,170 | 12/1985 | Chen et al. | 585/532 |
| 4,620,049 | 10/1986 | Schmidt et al. | 585/532 |

*Primary Examiner*—Curtis R. Davis
*Assistant Examiner*—J. Saba
*Attorney, Agent, or Firm*—Matthew R. Hooper; William H. Magidson; Ralph C. Medhurst

[57] ABSTRACT

Viscous, liquid polybutenes of at least 50 wt. % vinylidene content are disclosed together with a procedure for preparing the compounds using an aluminum chloride-organic nitro compound catalyst.

6 Claims, No Drawings

PROCESS FOR PREPARING POLYBUTENES WITH INCREASED REACTIVITY

FIELD OF THE INVENTION

The field of this invention relates to polybutenes with increased reactivity and to a method for producing these compounds. Specifically, the field of the invention relates to viscous, liquid polybutenes with increased reactivity which are prepared by means of a novel catalyst composition comprising $AlCl_3$ and a co-catalyst comprising an organic nitro compound. Resulting polybutenes have approximately at least a 50 wt. % vinylidene content. Polybutenes with approximately 50 wt. % vinylidene content react more readily with anhydrides to form compounds which have utility as additives for lubricants.

BACKGROUND OF THE INVENTION

Production of isobutylene polymers, called polybutenes, from mixed $C_4$ hydrocarbon feedstreams is generally known in the art. It is also known to utilize $AlCl_3$ as the polymerization catalyst in such processes and the prior art discloses a number of co-catalysts or catalyst promoters for use under various conditions in isobutylene polymerization. Organic nitro compounds are disclosed as components of catalyst systems for polymerization of olefins in concert with $AlCl_3$ and other components.

U.S. Pat. No. 3,629,222 discloses a process for production of solid, crystalline monoolefinic hydrocarbons such as highly crystalline polypropylene, the polybutenes and polystyrene. The process of the invention results in solid polymers having molecular weights greater than 1,000 and usually greater than 10,000, and can result in polymers of molecular weights of 1,000,000 or higher. The catalyst comprises (1) a compound selected from the group consisting of halides and lower alkoxides of a transition metal selected from the group consisting of titanium, zirconium, vanadium, chromium and molybdenum, (2) at least one component selected from the following: (a) a metal from Groups Ia, II or IIIa, or derivatives thereof; (b) organo-aluminum halides; and (c) a polymeric reaction product of aluminum and a methylene halide, and (3) a third component which can be an organic nitro compound such as nitrobenzene or 2-nitropropane. Polymers obtained by use of the above catalyst are characterized by unusually high crystallinity. There is no disclosure or teaching relevant to preparation of a viscous, liquid polymer characterized by a predominance of vinylidene structures, or use of a catalyst consisting essentially of aluminum chloride and an organic nitro compound.

U.S. Pat. No. 4,027,087 discloses a method for producing ethylene polymers in the presence of a catalyst prepared by using a metal carbonate or/and a metal hydrogen carbonate, a trivalent metal halide, such as $AlCl_3$, an aromatic compound such as nitrobenzene, a transition metal compound and an organoaluminum compound. The process is suitable for polymerizing alpha olefins other than ethylene but is particularly suitable for polymers of ethylene. The reference teaches all components of the catalyst are essential, that if any one is deficient, a highly active catalyst cannot be obtained.

U.S. Pat. No. 4,103,078 discloses a method for producing polymers of alpha olefins in the presence of a catalyst obtained by mixing an oxide of a metal of I, II, III, VII or VIII Group of the Periodic Table, or $SiO_2$ or $B_2O_3$, with a trivalent metal halide, such as $AlCl_3$, reacting the resultant mixture with a transition metal compound such as $TiCl_4$ in the presence of an aromatic compound such as xylene, and activating the resultant reaction product with an organoaluminum compound. The aromatic compound can be nitrobenzene. The monomer can be butene-1. The reference teaches that each component of the catalyst is an indispensable element if a polymerization catalyst with high activity is to be obtained. Polymerization of butene-1 yielded a white polymer of intrinsic viscosity in tetralin at 130° C. of 1.84. Conversion of butene-1 was 69%.

The prior art also discloses a number of co-catalysts, or catalyst promoters, with $AlCl_3$ for use under various conditions in isobutylene polymerization. A typical co-catalyst is hydrogen chloride. Representative disclosures include U.S. Pat. Nos. 3,200,169; 3,200,170; 3,997,129; 3,985,822; 3,119,884; and 4,558,170.

The present invention is considered distinguished from the foregoing references in that a viscous, liquid polybutene of approximately 50 wt. % vinylidene content is produced by a process wherein the catalyst and co-catalyst consist essentially of $AlCl_3$ and a liquid, organic nitro compound capable of solubilizing $AlCl_3$, selected from the group consisting of nitrobenzene, liquid alkyl-substituted nitrobenzene compounds, and aliphatic, liquid alkyl-substituted nitro compounds wherein the alkyl group has from 1 to 6 carbon atoms. Preferably, the aliphatic liquid alkyl-substituted nitro compounds are nitromethane, nitroethane, and nitropropane. The organic nitro compound is unreactive with aluminum chloride and does not neutralize the Lewis acid. The present invention is also considered distinguished from the foregoing references in that it produces a viscous, liquid polybutene which has a relatively high degree of reactivity with anhydrides, such as the reaction of polybutenes with maleic anhydride to produce polybutenylsuccinates.

Polybutenes produced by the process of this invention are characterized by a vinylidene distribution of at least 50 wt. %, and presence of approximately equal amounts of tri-substituted and tetra-substituted olefinic structures. Polybutenes produced by the method of this invention also demonstrate a weight average molecular weight, Mw, within the range of from about 1,000 to about 10,000, which is obtained without need for incremental process cooling facilities to control process temperature, as is required by prior art processes. The increased molecular weight obtained is especially advantageous in preparation of polybutylsuccinates. The higher molecular weight can impart viscosity index improving properties to the final products. The process is further notable in that (1) HCl is not used as a co-catalyst and that (2) the organic nitro compound co-catalyst solubilizes $AlCl_3$ and permits handling of the $AlCl_3$ catalyst as a fluid with attendant safeguards. It is equally notable as compared to the relative safeguards required by polmerization processes using boron trifluoride as a catalyst.

It has now been found that polymerization of a butane-butene stream can be carried out at a temperature within the range of from about $-20°$ C. to about $+50°$ C. at a pressure to maintain the feedstream in a liquid state wherein the resulting product has a vinylidene content of at least 50 wt. %.

It has now been found that use of a catalyst comprising aluminum trichloride and a liquid organic nitro compound capable of solubilizing $AlCl_3$, selected from the group consisting of nitrobenzene, liquid alkyl-substituted nitrobenzene compounds, and aliphatic, liquid alkyl-substituted nitro compounds wherein the alkyl group has from 1 to 6 carbon atoms, preferably nitromethane, nitroethane, or nitropropane, is effective for producing polybutene polymers containing at least 50% vinylidene structure and having a weight average molecular weight range from about 1,000 to about 10,000.

It has now been found that use of an aluminum trichloride and an organic nitro compound as catalyst is effective for producing a polybutene polymer having at least a 50% vinylidene content at a temperature within the range of from about $-20°$ C. to about $+50°$ C.

The present invention is based on the above discovery and relates to an improved method for producing a polybutene with improved unsaturated characteristics. The resulting product has increased vinylidene content and consequently greater utility as a chemical intermediate. Polybutene derivates are useful as additives to lubricants, for example, polybutenes which are reacted with maleic anhydride to prepare polybutenylsuccinate, a motor oil dispersant.

SUMMARY

An unsaturated viscous, liquid polybutene polymer is disclosed. The unsaturated polymer has a vinylidene content of at least 50 wt. % and a weight average molecular weight within the range of from about 1,000 to about 10,000. These polybutenes have increased vinylidene content and react readily with anhydrides to form compounds which have utility as additives for lubricants. The polybutenes with increased unsaturation are prepared by polymerizing a butane-butene stream in the presence of $AlCl_3$ and a co-catalyst selected from the group consisting of nitrobenzene, liquid alkyl-substituted nitrobenzene compounds, and aliphatic, liquid alkyl-substituted nitro compounds wherein the alkyl group has from 1 to 6 carbon atoms, preferably nitromethane, nitroethane, or nitropropane. Reaction temperature is in the range of from about $-20°$ C. to about $+50°$ C.

DETAILS OF THE INVENTION

According to the present invention, there is provided a polybutene composition with increased unsaturation, having a vinylidene content of at least 50 wt. %, and a process for preparing the compound. The term vinylidene is defined as referring to an unsaturated molecular structure containing a di-substituted double bond wherein the double bond is located between the terminal carbon of an alkyl group and the rest of the molecule.

In accordance with the present invention, there has been discovered a continuous process for preparing medium range molecular weight polybutene having a weight average Mw in the range of from about 1,000 to 10,000 and a vinylidene content of at least 50 wt. % from a feedstream mixture of $C_4$ hydrocarbons containing at least 6 wt. % isobutylene in a continuous stirred reactor at a reaction temperature of about $-20°$ C. to about $+50°$ C., said reactor having a feedstream inlet and a catalyst $AlCl_3$ plus organic nitro compound inlet, which is separate from the feedstream inlet, and introducing into the reactor the isobutylene feedstream and catalyst, whereby polymerization occurs to form polybutene in the reaction mixture. The reaction mixture is withdrawn from the reactor and quenched with water. The polybutene product is separated therefrom by stripping and other conventional procedures.

The organic nitro compound, $RNO_2$, can be selected from the group consisting of nitrobenzene, liquid alkyl-substituted nitrobenzene compounds, and aliphatic, liquid alkyl-substituted nitro compounds wherein the alkyl group has from 1 to 6 carbon atoms, and is preferably nitromethane, nitroethane, or nitropropane. It is essential that the liquid organic nitro compound be unreactive with aluminum chloride and not neutralize the Lewis acid.

The $AlCl_3$-$RNO_2$ catalyst system is a homogeneous catalyst and is not a slurry system. The $AlCl_3$-$RNO_2$ catalyst therefore permits a more accurate method of adding catalyst to the reactor, i.e. by a liquid metering method.

The instant invented process can be operated in the continuous or batch method.

The feedstock for the process of this invention is a mixture of pressure liquified $C_4$ hydrocarbons such as catalytic cracked $C_4$ or stream cracked $C_4$ fractions which contain at least about 6 wt. % up to about 50 wt. % isobutylene together with butene-1, cis- and trans-butene-2, n-butene, isobutane and less than about 1% butadiene. The preferred $C_4$ feedstream is derived from refinery catalytic or steam cracking and contains about 6–45 wt. % by weight isobutylene, about 25–35 wt. % saturated butanes and about 15–50 wt. % 1- and 2-butenes. The $C_4$ products other than isobutylene function as the reaction medium.

Typical composition of an olefin butane-butene feed for preparation of polybutene is as follows:

| Component | Weight % |
|---|---|
| isobutane | 4.1 |
| n-butane | 7.2 |
| 1-butene | 23.4 |
| isobutylene | 43.9 |
| trans-2-butene | 11.8 |
| cis-2-butene | 9.6 |

The polybutene prepared in accordance with this invention offers a number of advantages over polybutene prepared by prior art methods with respect to those properties which are important for its use, especially in a form of reaction product suitable for the preparation of polybutenylsuccinate. The polymer has a different olefin distribution than polymer produced by other $AlCl_3$ catalyst systems. The molecular weight of the polymer produced by the instant method can be higher at a given process temperature than polymer prepared by other $AlCl_3$ catalyst systems.

The significant aspects of this invention are that the invention provides a novel composition of matter comprising a polybutene containing a high degree of a viscous, liquid vinylidene structure, at least 50 wt. %, with a weight average molecular weight within the range of from about 1,000 to 10,000. The high percentage of vinylidene structure aids substantially in the reactivity of the compound. This olefin distribution substantially increases the polybutene conversion to compounds useful as lubricant additives by eliminating steric constraints. The high molecular weight range is advantageous for processing or manufacture of the polymer. This catalyst demonstrates that heavy molecular weight polymers, typically used as lubricant dispersant applications, can be produced at temperatures without requiring refrigeration.

In practice of this invention, the amount of AlCl$_3$ which is used in the polymerization is suitably 0.02 wt. % to 0.20 wt. %, preferably 0.06 wt. % to 0.15 wt. %, based on total feed to be polymerized. The AlCl$_3$ is in a solution of from 2.3 wt. % to about 57 wt. % AlCl$_3$ in organic nitro compound, preferably nitromethane, nitroethane, nitropropane or nitrobenzene, which is then added to the reactor. Nitrobenzene is more preferred. Nitropropane can require safety measures which can increase the economic cost of the process. The instant invention is also applicable to any feed composition which contains C$_3$–C$_5$ paraffins, olefins or diolefins.

In summary, the instant invention comprises a process for preparation of viscous, liquid polybutene polymers having a vinylidene content of at least 50 wt. % and of a weight average molecular weight of from about 1,000 to about 10,000, which process comprises: a) feeding a butane-butene stream into a suitable reactor at a reaction temperature within the range of from about −20° C. to about 50° C. at a pressure to maintain said feedstream in a liquid state; b) feeding into said reactor a catalyst consisting essentially of AlCl$_3$ and a liquid organic nitro compound, which is unreactive with aluminum chloride and does not neutralize the Lewis acid, wherein said AlCl$_3$ is solubilized in said liquid organic nitro compound to form a homogeneous catalyst; c) polymerizing butenes of said butane-butene stream in the presence of said catalyst to prepare a polybutene having at least 50 wt. % vinylidene structure and a weight average molecular weight in the range of from about 1,000 to 10,000; and d) separating said polybutene from said reaction mixture. The instant invention further comprises the polybutene prepared by the instant invented process. The said liquid organic nitro compound is selected from the group consisting of nitrobenzene; liquid alkyl-substituted nitrobenzene compounds; and aliphatic, liquid alkyl-substituted nitro compounds wherein the alkyl group has from 1 to 6 carbon atoms. Preferably, the liquid organic nitro compound is selected from the group consisting of nitromethane, nitroethane, nitropropane and nitrobenzene. More preferably, the liquid organic nitro compound is nitrobenzene. The AlCl$_3$ solubilized in said liquid organic nitro compound is present in a range of from about 2.3 wt. % to about 57 wt. % of the weight of the AlCl$_3$ plus the organic nitro compound. The AlCl$_3$ is present in said catalyst in an amount of from 0.02 wt. % to about 0.20 wt. % of total weight of said butane-butene stream. Preferably, the AlCl$_3$ present in the catalyst is an amount of from 0.06 wt. % to about 0.15 wt. % of the total weight of the butane-butene stream.

The following examples illustrate the process and compositions of the instant invention but are not to be construed as limiting the scope of the invention.

Example I illustrates that the weight percent of vinylidene structure of the polybutene obtained by the process of the instant invention is at least 50 wt. %. Example II illustrates that the weight percent of a vinylidene structure obtained by a process using an aluminum chloride catalyst is significantly less than that obtained by the process of the instant invention, and is comparable to the vinylidene content of a commercially available polybutene. Example III illustrates the increased reactivity obtained with polybutenes of greater vinylidene content. Examples IV to VII illustrate that molecular weight obtained with the process of the instant invention is within the range of 1,000 to 10,000. Examples IV to VII also illustrate that a higher molecular weight polymer is obtained for the same amount of catalyst added, i.e., higher molecular weight polymers can be made with AlCl$_3$-RNO$_2$ as catalyst than with AlCl$_3$.

EXAMPLE I

In a dry septum sealed bottle a pre-mixture of AlCl$_3$-nitrobenzene catalyst was prepared by adding 1.2042 grams AlCl$_3$ to 50.0 grams nitrobenzene. The reaction vessel was a 12 oz. Fischer Porter bottle equipped with a magnetic stirrer, a nitrogen inlet, isobutylene inlet and various outlets. To this vessel was first added 6.2 ml of the above catalyst, equivalent to 0.1758 grams of AlCl$_3$, and then 165 grams of 20% isobutylene and 80% isobutane feed.

The reaction was carried out for one hour at 32° F. as maintained by an ice bath around the outside of the reaction bottle. After exactly one hour the reaction vessel was vented of any unreacted B-B feed and the reaction quenched with 50 ml of deionized water. The water killed the catalyst and removed the AlCl$_3$ from the polymer. After separation of the water from the polymer, the polymer was dissolved in approximately 50 ml of hexane and dried over anhydrous MgSO$_4$. Next the solvent, hexane, was removed from the polymer via a rotoevaporator under conditions of 60° C. and a vacuum of 29 inches of Hg. The polymer was then submitted for $^{13}$C NMR analysis to determine the olefin distribution. Estimated number average molecular weight by $^{13}$C NMR analysis was approximately 900. Vinylidene content was 54.2 wt. %. These data are shown in Table I.

EXAMPLE II

The procedure of Example I was repeated except for the following changes in reactants: 0.038 grams AlCl$_3$ slurried in 10 ml of CH$_2$Cl$_2$ was used as the catalyst. Vinylidene content was 4.1 wt. %. Number average molecular weight was 869. The $^{13}$C NMR olefin distribution data is shown in Table I. Olefin distribution data for a commercially available polybutene of approximately 920 number average molecular weight is also shown. The commerically available polybutene is AMOCO Polybutene H-100, Amoco Chemical Company, Chicago, Illinois.

TABLE I

| Polymer | Olefin Distribution - Polybutenes | | | |
| --- | --- | --- | --- | --- |
| | wt. % I | wt. % II | wt. % III | wt. % IV |
| Example I | 54.2 | 11.9 | 12.8 | 21.1 |
| Example II | 4.1 | 73.0 | 0.0 | 22.9 |
| H-100 Polybutene | 5.5 | 72.9 | 0.0 | 21.6 |

Notes:
I = Vinylidene
II = Tri-substituted
III = Tri-substituted
IV = Tetra-substituted
wt. % Olefin types determined by $^{13}$C NMR.

EXAMPLE III

The following example illustrates the increased reactivity of polybutene polymers with increased vinylidene content relative to the reactivity of polybutene polymers with lower vinylidene content. Polybutene polymers with increased vinylidene content were reacted with maleic anhydride. Typical reaction conditions in a conventional method involve combining the polybutene and maleic anhydride in a 1.0 to 1.1 mole ratio, respectively. This mixture is then allowed to react for 6 hours at 245° C. The reactivity or yield of polyisobutylene succinic anhydride is determined by column chromatography utilizing silica gel.

Two samples of polybutene polymer were prepared of approximately 950 number average molecular weight, one with a vinylidene content of 59.6 wt. %, the other with vinylidene content of 5.5 wt. %. Each sample was reacted with maleic anhydride (MAN) by conventional method. Reactivity with maleic anhydride was measured by column chromatography. Maleic anhydride reactivity with polybutene A with vinylidene content of 59.6 wt. % was 68.3%, reactivity with polybutene B with vinylidene content of 5.5 wt. % was 63.4%. Maleic anhydride reactivity with polybutene A was 7.7% greater than with polybutene B. Data are in Table II under Part A.

Two samples of polybutene, polybutenes C and D, of higher molecular weight than polybutenes A and B, were prepared. Number average molecular weights were 1235 and 1279, respectively. Vinylidene contents were 82.7 and 11.7 wt. %, respectively. Maleic anhydride reactivity of polybutene C was 16.6% greater than with polybutene D. Data are in Table II under Part B.

TABLE II

Reactivity-Maleic Anhydride with Polybutene

| Polybutene | Mol. Wt. | Vinylidene Wt. % | Reactivity MAN-% | Increase % |
|---|---|---|---|---|
| | | Part A | | |
| A | 957 | 59.6 | 68.3 | 7.7 |
| B | 970 | 5.5 | 63.4 | — |
| | | Part B | | |
| C | 1235 | 82.7 | 67.3 | 16.6 |
| D | 1279 | 11.7 | 57.7 | — |

Note: Mol. Wt. by vapor pressure osmometry

EXAMPLE IV

A two-liter stainless steel autoclave equipped with an overhead stirrer, cooling coils, a butane-butene feed inlet and an inlet for catalyst addition was the reactor. To the reactor there was added 680 grams of butane-butene feed and 2.0 grams $AlCl_3$ dissolved in 5.2 grams nitromethane. The nitromethane had been previously dried over 3Å molecular sieves. Upon addition of the feed and catalyst, an initial exotherm to 73° F. occurred for a period of 25 seconds. The reaction was then maintained at a temperature of 50° F. for a 60 minute reaction period. Following the reaction, the unreactive B-B feed was vented and the reactor quenched with water to remove the remaining $AlCl_3$. The water was then separated from the polymer by extraction techniques. The polymer was diluted in pentane and passed through a silica gel column to dry the polymer. The polymer was then analyzed by gel permeation chromatography (GPC) to determine molecular weight. Weight average molecular weight was 7863.

EXAMPLE V

The procedure of Example IV was repeated except that 2.0 grams $AlCl_3$ was dissolved in 10 grams of 2-nitropropane. Weight average molecular weight of the resulting polymer was 9123, as determined by gel permeation chromatography (GPC).

EXAMPLE VI

The procedure of Example IV was repeated except that 2.0 grams $AlCl_3$ was dissolved in 10 grams of nitrobenzene. Weight average molecular weight was 8119 by gel permeation chromatography (GPC).

EXAMPLE VII

The procedure of Example IV was repeated except that 1.0 grams $AlCl_3$ was dissolved in 10 ml of hexane. Weight average molecular weight by GPC was 5985.

What is claimed is:

1. A process for preparation for viscous, liquid polybutene polymers with increased reactivity which have a vinylidene structure of at least 50 wt. % and are of a weight average molecular weight of from about 1,000 to about 10,000, which process comprises:
   (a) feeding a butane-butene stream into a suitable reactor at a reaction temperature within the range of from about −20° C. to about +50° C., at a pressure to maintain said feedstream in a liquid state;
   (b) feeding into said reactor a catalyst consisting essentially of $AlCl_3$ and a liquid organic nitro compound which is unreactive with said aluminum chloride and does not neutralize the Lewis acid, wherein said $AlCl_3$ of said catalyst is present in a range of from about 0.02 wt. % to about 0.20 wt. % of total weight of said butane-butene stream, wherein said $AlCl_3$ is solubilized in said liquid organic nitro compound to form a homogeneous catalyst and said $AlCl_3$ solubilized in said liquid organic nitro compound is present in a range of from about 2.3 wt. % to about 57 wt. % of the weight of $AlCl_3$ plus said organic nitro compound;
   (c) polymerizing butenes of said butane-butene stream in the presence of said catalyst to prepare a polybutene having at least 50 wt. % vinylidene structure and a weight average molecular weight in the range of from about 1,000 to 10,000; and
   (d) separating said polybutene from said reaction mixture.

2. The polybutene prepared by the process of claim 1.

3. The process of claim 1 wherein said organic nitro compound is selected from the group consisting of nitrobenzene; liquid alkyl-substituted nitrobenzene compounds; and aliphatic, liquid alkyl-substituted nitrobenzene compounds; wherein the alkyl group has from 1 to 6 carbon atoms.

4. The process of claim 1 wherein said organic nitro compound is selected from the group consisting of nitromethane, nitroethane, nitropropane, and nitrobenzene.

5. The process of claim 1 wherein said organic nitro compound is nitrobenzene.

6. The process of claim 1 wherein said $AlCl_3$ is present in said catalyst from about 0.06 wt. % to about 0.15 wt. % of the total weight of said butane-butene stream.

* * * * *